(12) United States Patent
Gutierrez-Uribe et al.

(10) Patent No.: US 8,470,858 B2
(45) Date of Patent: Jun. 25, 2013

(54) AGAVE SYRUP EXTRACT HAVING ANTICANCER ACTIVITY

(75) Inventors: Janet-Alejandra Gutierrez-Uribe, Monterrey (MX); Sergio Serna-Saldivar, San Pedro Garza Garcia (MX)

(73) Assignee: Albino Vargas Ozuna, Nuevo Leon (MX)

( * ) Notice: Subject to any disclaimer, the term of this patent is extended or adjusted under 35 U.S.C. 154(b) by 741 days.

(21) Appl. No.: 12/206,776

(22) Filed: Sep. 9, 2008

(65) Prior Publication Data
US 2009/0124685 A1    May 14, 2009

(51) Int. Cl.
*A01N 43/40*    (2006.01)
*A01N 43/16*    (2006.01)
*A61K 31/44*    (2006.01)
*A61K 31/35*    (2006.01)

(52) U.S. Cl.
USPC .......................................... 514/350; 514/456

(58) Field of Classification Search
USPC ................................................ 514/350, 456
See application file for complete search history.

(56) References Cited

U.S. PATENT DOCUMENTS

| | | | | |
|---|---|---|---|---|
| 2,895,953 | A | * | 7/1959 | Wall et al. ....................... 536/6.3 |
| 2,991,282 | A | * | 7/1961 | Rubin ............................. 540/18 |
| 3,895,999 | A | * | 7/1975 | Loken ........................... 435/165 |

OTHER PUBLICATIONS

Gutierrez et al. Industrial Crops and Products, 2008, vol. 28, pp. 81-87.*
Starkman, A. Mezcal in Oaxaca, Published online May 2007, pp. 1-4.*
Garcia et al. Fitoterapia, 1999, vol. 70, pp. 71-73.*

* cited by examiner

*Primary Examiner* — Samira Jean-Louis
(74) *Attorney, Agent, or Firm* — Young & Thompson

(57) ABSTRACT

The present invention comprises an *agave* syrup stored for at least eight weeks, having phytochemicals preferably selected from the group comprising flavonoids, polycosanols and sapogenins, which provide anticancerigen and antioxidant properties to the *agave* syrup. It is also described an extract of said *agave* syrup and a related method for its extraction and application for inhibiting the growth of cancer cells.

10 Claims, 10 Drawing Sheets

5,7-Dihydroxy-6,5'-dimethoxy-3',4'-methylenedioxyflavanone

AGAVE SYRUP EXTRACT HAVING ANTICANCER ACTIVITY

BACKGROUND OF THE INVENTION

A. Field of the Invention

The present invention is related to processes or methods to obtain extracts from *agave* syrup containing various phytochemicals such as polyphenols, flavonoids, saponins, phytosterols, steroids, triterpens, polycosanols and other natural products having proved antioxidant properties and more particularly to a method for using an *agave* syrup extract as an antioxidant, food supplement or as an anti-neoplasic, anti-carcinogenic or anti-tumoral preparation for the prevention or inhibition of growing cancers or the growth of cancer cells, such as tumors or hormone-dependent or independent cancerigen cells, from breast, prostate or liver.

B. Description of Related Art

According to anthropologists, México is the original source of the *agave* plant (*Agave* spp). Said plant has been used since remote times as a food source, forage, medicine, as a fiber source (henequen, wild lettuce) and as a building material among other uses. In Mesoamerica humans have always considered the importance of this plant since at least 9000 years.

Indigenous people gradually selected the sweetest *agaves* since they cooked the plants inside earth holes having a bed of basalt rocks and stored them for future use. Mexican indigenous civilizations described 14 different kinds of *agave*. The Mexoxochitli *agave* corresponds to the American *Agave* species.

Some *agaves* were used for curing ataxia; other *agaves* were used to reestablish the health in women, especially after delivery and for treating articulation pains. *Agave* leaves were also used for preventing scorbute and for the healing of injuries. Its main use was for the elaboration of alcoholic beverages such as pulque, mezcal, bacanora and tequila, which is produced from the *Agave tequilana* plant.

Taxonomically, the *Agave* genus pertains to the Agavaceae family. There are approximately 310 species of *Agave* known in the American Continent, from which 272 are found in Méexico, which led to consider Mexico as the cytogenetic origin of this important plant. The main characteristic of the *Agave* plant is its optimum adaptation to the arid conditions of Mesoamerica and Aridamerica. The plant pertains to the monocotiledonia group and to the lilacea order, which produce big and branched roots, succulent leaves having sunken stomas and has a photosynthetic metabolism which allows the plant to adapt to low water conditions and to take advantage of the carbon dioxide more efficiently (Granados Sánchez 1994). The chromosomic number of the Americana *Agave* is 2n=60.

The aguamiel or the *Agave* sweet extract is considered as an important beverage since it has a good nutrimental value, supplies energy, and is rich in essential amino acids essential for human growth. The aguamiel is a colorless, transparent liquid having a very sweet and pleasant flavor. It has a density of 1.049 g/cc and a total sugar content of approximately 10%. More of the 90% of the sugar content comprises sucrose (Granados Sánchez, 1994).

The vegetal material, aguamiel and syrup from the different *agave* kinds have been used since ancestral times for treating many maladies, specially for the prevention and treatment of diabetes, skin diseases as a scarring promoter, arthritis and cardiovascular diseases. However, the possible substances and compounds involved in the above referred biologic effects of the aguamiel are not very well known.

One of the possible action mechanisms may be related to the antioxidant activity, which has not yet been measured for the aguamiel. It is only known that the raw *agave* has an antioxidant capacity of 12.48 µmols trolox equivalent (ET)/g and that such value is increased to 29.38 when the *agave* is boiled (Wu and collaborators, 2004).

There also exist several patents related to the fructooligosaccharides (FOS) or inulin extraction from the soluble dietetic fiber. Said compounds are considered to have prebiotic, anticholesterolemic and antidiabetic effects.

In addition to the inulin the sapogenins have been an extensively researched *agave* compound family (Yang and col., 2006, Blunden and col., 1980, Blunden and col., 1986, Sharua and Khanna, 1980, Jin, Liu and Yang, 2003). Jin, Zhang and Yang (2004), found three new steroidal saponins (agamenosides H-J) and a new agavegenin together with six known steroids present in the residue coming from the separation of the fibers of the A. American leaves which are used in the fiber industry in China.

The steroidal saponins present in the *Agave* have shown to have anti-inflammatory properties which can potentially help to prevent and/or treat cancer. Da Silva and collaborators (2002) demonstrated the anti-inflammatory properties of a steroidal saponin extracted from *Agave attenuate*. Said steroidal saponin didn't shown the hemolytic activity shown by other saponins due to the greater affinity of the steroids for cholesterol at the erythrocytes membrane. The saponins from *Dracaena surculosa*, which is a plant from the Agavaceae family have been tested in vitro in order to determine its activity in leukemia promyelocytic human cells (HL-60) and only three out of 9 saponins shown a slightly cytotoxic activity (Yokosuka, Mimaki y Sashida, 2000).

Additionally, there has been reported the presence of flavonoids in the *agave*. The agamennone was the first flavonoid reported in the *agave* (Parmar and col., 1992). Subsequently, there have been found other three related flavonoids (Tinto and col. 2005). However, it hasn't been proved any biologic activity by said compounds neither its anticancerigen activity. Until now, all the reported activity related to *agave* syrups has been attributed to the inulin or to the sapogenins.

Japanese patent JP 11049687 claims a cutaneous preparation made of extracts from different *Agave* plants for external use, which stimulates the retention of water and inhibit the melamine production and thus, it is useful for dermatitis, to prevent oily skin, acne and dandruff. The Aloe Vera juice has been claimed for the treatment of mastitis in domestic cattle and for many useful common use products such as shampoos, creams for the skin, etc.

Mexican patent application of Meixueiro Valverde PCT/MX2004/0000417 disclose the production of an *Agave* liquid extract having anticancerigen and antiviral properties (virus sincitial of the subgroup of the Moxovirus) and that may be used as a cellular and glandular reconstituent in humans as well as in domestic animals. The extract can be used for treating asthma, sinusitis, tonsillitis, mycotic infections and intestinal parasites. The inventor relates the positive effects to phytochemical compounds having a proteinic nature which are obtained from the agavacea plant fleshy leaf cuticle and salvia. The method for the obtention of the extract comprises harvesting the *agave* fleshy leafs having from 4 to 15 years old; boiling the fleshy leafs for a time of from 20 to 180 minutes in water at a temperature of from 70 to 100° C. (with a water-fleshy leafs relation of 2 to 4:1); grinding the boiled fleshy leafs and filtering the resulting liquid. The extract itself comprises the viscous greyish green filtered matter having a solid content of 5%. The raw extracts from two tested *agaves* (alone and combined) had a good anticancerigen activity in vitro. However the inventor didn't carry out any kind of analysis in order to find which phytochemical compounds may have anticancerigen and antiviral potential. Furthermore, the related art does not disclose the anticancerigen activity of the *agave* syrup which was found by the applicant.

The use of the *agave* syrup extracts provides a source of active ingredients—not used until now—, which can be prepared and administered in a suitable way in many ways, including the treatment of cancer.

Applicant discovered that several kinds of phytochemicals from *agave* syrup or its extracts have potential synergic effects such as inhibiting cancer cells and or providing antioxidant effects.

Therefore, applicant developed an *agave* syrup extract composition (*Agave* spp) from several *Agave* varieties such as *A. atrovirens, A salmiana, A. lehmanni* and a related method comprising the use of its components alone or combined with other known and effective nutraceutic compounds such as vitamins A, C, and E, and/or sources of selenium for inhibiting the growth of cancer cells and/or providing an antioxidant effect.

The *agave* syrup extract composition of the present invention inhibits the growth of cancer cells and has antioxidant effects, for example, as an active ingredient in a food supplement and/or foods, cosmetics or medicines, or it may be an active ingredient in antineoplastic, anticancerigen or antitumoral preparations, for treating as well as preventing cancer or inhibiting the growth of cancer cells, such as hormone dependent or independent tumors such as breast, prostate, colon or liver cancer.

The *agave* syrup extract composition of the present invention comprises partially purified extracts derived from *agave* syrup which contain saponins, phytosterols, total phenolic compounds such as polyphenols, flavonoids and tannins which have a high antioxidant activity. Said extracts may be partially or totally purified by chromatography and/or other physic and/or chemical and/or bioseparation methods and be fractionated by a fast centrifugal partition chromatography.

The extracts may be mixed with two or more carriers, excipients and/or diluents pharmaceutically or veterinary acceptable.

The invention further comprises the isolated or purified compounds obtained from *agave* syrup. Said compounds are useful in an isolated way or combined at several concentrations. The compounds may be synthetically obtained as well as by its modification by several chemical and/or enzymatic processes.

SUMMARY OF THE INVENTION

It is therefore a main object of the present invention to provide an *agave* syrup extract composition (*Agave* spp) from several *Agave* varieties such as *A. atrovirens, A salmiana, A. lehmanni* useful for inhibiting the growth of cancer cells and/or providing an antioxidant effect.

It is an additional object of the present invention to provide a method comprising the use of components and combinations of an *agave* syrup extract composition (*Agave* spp) from several *Agave* varieties such as *A. atrovirens, A salmiana, A. lehmanni* alone or combined with other known and effective nutraceutical compounds such as vitamins A, C, and E, and/or sources of selenium for inhibiting the growth of cancer cells and/or providing an antioxidant effect.

It is yet a main object of the present invention, to provide an *agave* syrup extract composition of the above referred nature which may be used as an active ingredient in a food supplement and/or foods, cosmetics or medicines, or it may be an active ingredient in antineoplastic, anticancerigen or antitumoral preparations, for treating as well as preventing cancer or inhibiting the growth of cancer cells, such as hormone dependent or independent tumors such as breast, prostate, colon or liver cancer.

It is still a main object of the present invention, to provide an *agave* syrup extract composition of the above referred nature, which comprises partially purified extracts derived from *agave* syrup which contain saponins, phytosterols, total phenolic compounds such as polyphenols, flavonoids and tannins which have a high antioxidant activity. Said extracts may be partially or totally purified by chromatography and/or other physic and/or chemical and/or bioseparation methods and be fractionated by a fast centrifugal partition chromatography.

It is another main object of the present invention to provide an *agave* syrup extract composition of the above referred nature which may be mixed with two or more carriers, excipients and/or diluents pharmaceutically or veterinary acceptable.

These and other objects and advantages of the present invention will become apparent to those persons having an ordinary skill in the art, from the following detailed description of the invention which will be made with reference to the accompanying drawings.

DETAILED DESCRIPTION OF THE INVENTION

Inventors discovered that the *agave* syrup activity increases in function of the storing time of the processed product and that there are flavonoids, polycosanols and sapogenins present in said product which are responsible for the anticancerigen activity.

The invention will be now described making reference to the following examples and the accompanying drawings.

The description and examples refer to the methods and steps for using the present invention concerning to the *agave* selection in terms of concentration and bioactivity of a given variety of *agave* in order to derivate the most useful use of the extracts and of the compounds present in any given variety for treating or preventing several kinds of cancer as well as the various ways in which said extracts can be administered in order to achieve the object of the present invention. Although the description and examples refer to certain Mexican *agave* varieties used by the inventors in their research and conception of the invention, it will be evident for persons skilled in the art that any other *agave* variety will be included in the scope of the invention.

EXAMPLE 1

An *agave* syrup was obtained by boiling approximately 10 liters of aguamiel during 5-6 hours until obtaining approximately 1 liter of syrup having 70% of solids, which is stable at ambient conditions and resistant to microbial attacks. The aguamiel is extracted from *agaves* which are near florescence. The *agave* is cut (the floral tail is destroyed and a cavity is formed in which the sap or aguamiel is deposited). The cavity is covered with parts of the same maguey in order to avoid animal attacks. Subsequently, the aguamiel is recollected by scratching the maguey in order to stimulate the production of sap.

EXAMPLE 2

Antioxidant capacity and anticancerigen effect of *agave* syrup extracts stored for more than six months at ambient temperature.

In order to obtain an extract, 4 to 5 g of *agave* syrup produced in Example 1 stored for more than 6 months were mixed with 10 ml of 80% methanol. Subsequently the mix was centrifuged for 5 minutes at 1,000 rpm. The supernatant antioxidant activity was evaluated by means of the ORAC method giving a value of 61.87±4.02 μmols TROLOX equivalents/g sample. The anticancerigen activity in vitro was also evaluated using human colon cancer cells cultivations (Caco-2), breast cancer cells (MCF7), and liver cancer cells (HepG2). The growth inhibition percentage values were obtained using 15 mg/ml (syrup/cultivation media). It was observed that there was no significant effect over the growth of breast cancer cells. However, the growth of colon cancer cells was inhibited by 84.89±0.29 and the growth of liver cells was inhibited by 67.95±4.87.

EXAMPLE 3

Evaluation of the effect of solvent over the extraction of anticancerigen compounds from *agave* syrup.

Figure 1:
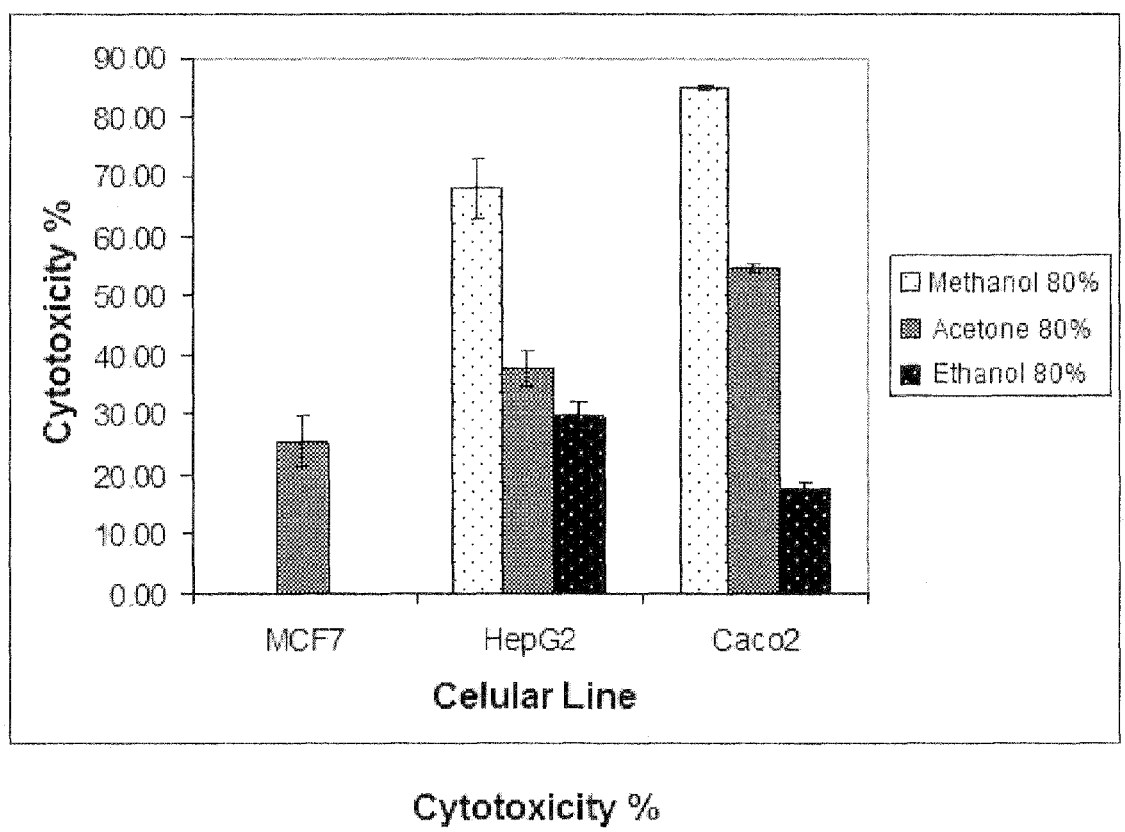
FIG. 1 comprises a graphic showing a comparison between the cytoxicity exerted over three cellular lines of human cancer from extracts obtained with methanol, acetone or ethanol at an 80% in water from *agave* syrup stored for more than three months.

As in Example 2, in order to obtain an extract, there were taken from 4 to 5 g of *agave* syrup produced in Example 1 stored for more than 6 months, which were mixed with 10 ml of methanol, acetone or ethanol at an 80% in water. Subsequently the mix was centrifuged and the supernatant antioxidant activity over human cancer cellular lines described in Example 2 was determined, FIG. 1 shows that methanol at an 80% is the best solvent for the extraction of *agave* syrup compounds having anticancerigen activity. The acetone is the second best solvent for the extraction of *agave* syrup compounds and it was the only solvent by which applicant was capable of obtaining supernatants having inhibitory growth activity of breast cancer cells (MCF-7). With regard to the supernatants obtained by ethanol at an 80%, it was observed inhibitory growth activity of colon and liver cancer cells only. However, the observed activity of the extracts obtained by methanol was less than half of the observed activity of the extracts obtained by methanol.

EXAMPLE 4

Tested *agave* varieties and determination of the optimum storing time before extraction.

In accordance with consumer subjective observations there was recognized the possibility that the *agave* syrup could have nutraceutical activity. Applicant considered of great importance to know about the effects that the storing time has over the breast, colon and liver cancer cell growth inhibitory activity. At the same time, there was evaluated the effects of several *agave* plants coming from different places in order to determine if the place of origin has any significance over the overall effects of the plant.

Figure 2:
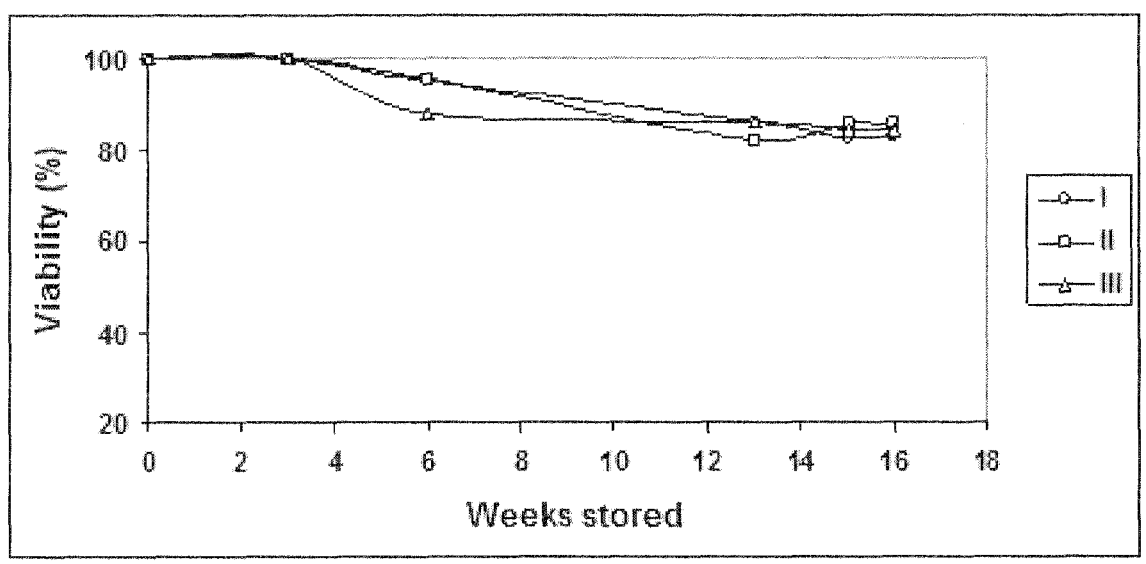
FIG. 2 comprises a graphic that show the effect of the storing period at ambient temperature in three samples of *agave* syrup coming from different places over the anticancerigen activity in hormone dependent breast cancer cells (MCF7) considering the viability percentage decrease.

There were tested 3 *agave* syrups obtained from different places, and their extracts were obtained by methanol at an 80% as described in Examples 2. FIG. 2 shows that breast cancer cells maintain a viability percentage greater than 90% if there are used extracts from *agave* syrup stored by less than six months. However, viability percentages didn't come down from 80% even when there were used *agave* extracts stored for approximately 4 months.

Figure 3:
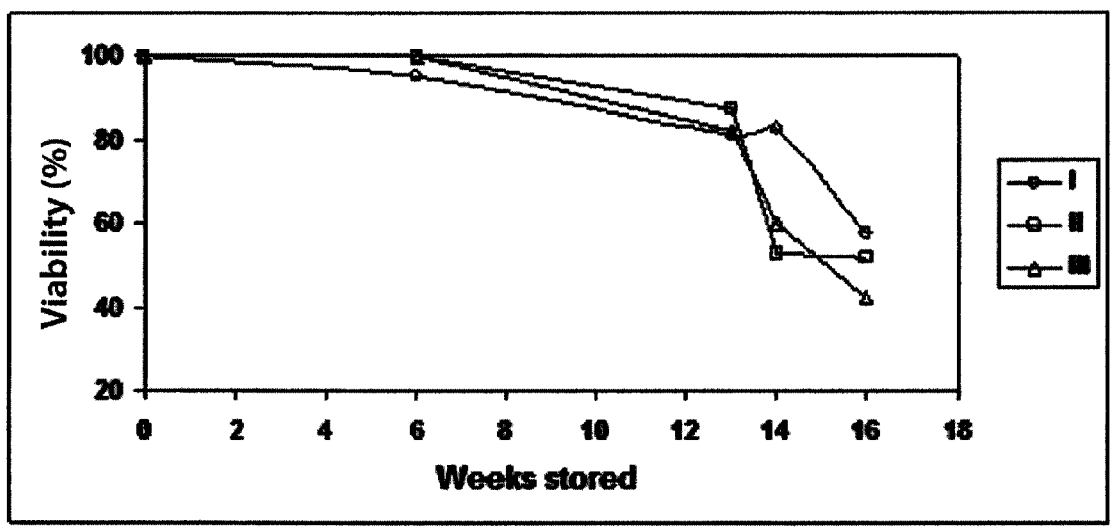
FIG. 3 comprises a graphic showing the effect of the storing period effect at ambient temperature in three samples of *agave* syrup coming from different places over the anticancerigen activity in colon cancer cells (Caco2) considering the viability percentage decrease.

With regard to colon cancer, FIG. 3 comprises a graphic that shows the decrease of the cellular viability with respect to the storing period of the used *agave* syrup. The graphic show that it is necessary to store the *agave* syrup for more than eight weeks in order to obtain significant effects. The *agave* syrups obtained from three different places, decreased the cellular viability to approximately 50% after being stored for approximately four months.

Figure 4:
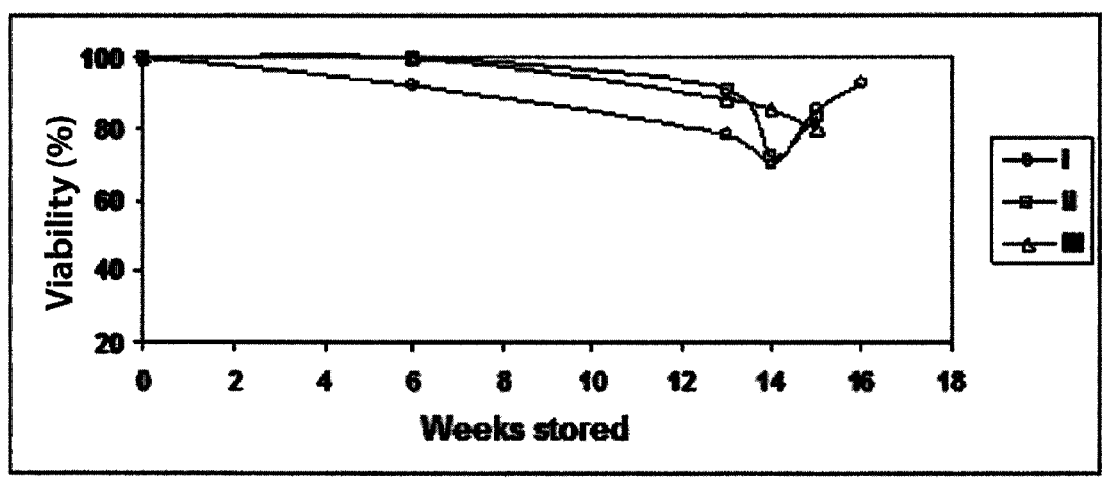
FIG. 4 comprises a graphic showing the effect of the storing period effect at ambient temperature in three samples of *agave* syrup coming from different places over the anticancerigen activity in liver cancer cells (HepG2) considering the viability percentage decrease.

Additionally, the effect of the extracts over the liver cancer cells which are shown in FIG. 4 with respect to the storing period of the *agave* syrup, appears to be the same for the breast cancer cells.

Therefore, applicant deduced that the *agave* syrup must be stored for at least 16 weeks in order to extract the active ingredients. Furthermore, it was evident that the compounds which have activity over the liver cancer cells require more time to be modified by mechanisms intrinsic to the product during the storing period.

EXAMPLE 5

Separation by Fast Centrifugal Partition Chromatography

Figure 5:
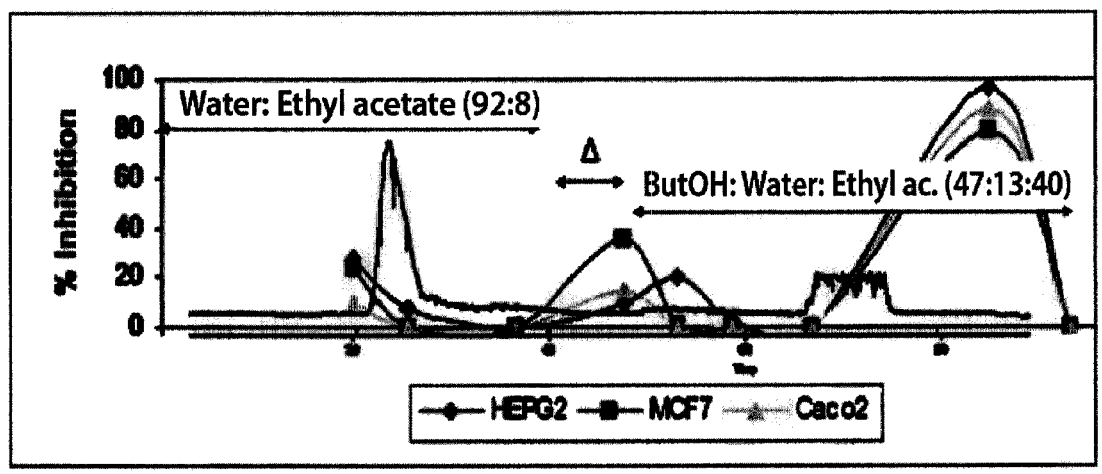
FIG. 5 comprises a graphic showing the result of the screening of compounds having anticancerigen activity obtained from an *agave* syrup extract obtained by 80% methanol and separated by means of a fast centrifugal partition chromatography together with a solvent system comprised by water:ethyl acetate (92:2) and butanol water:ethyl acetate (47:13:40).

In order to found the active compounds of the *agave* syrup, it was performed a fast centrifugal partition chromatography using a Kromatron equipment (France) using a 1 liter column. A mix of butanol:water:ethyl acetate (47:13:40) was used as a stationary phase in order to extract most of the sugars of the *agave* syrup using water:ethyl acetate (92:8) as a mobile phase. There was injected 5 g of syrup dissolved in 20 ml of the mobile phase. FIG. 5 shows that the obtained chromatogram at 260 nm has a peak between the minute 20 to 25 which corresponds to the sugars extracted from the *agave* syrup which are the main compounds of the *agave* syrup. However the maximum activity peak can be found in the analysis of the last fractions showing the lipophilic characteristics of the product active compounds. It must be emphasized that the fractions were tested at a concentration of 0.5 mg/ml (fraction/mammal cells cultivating medium).

The conditions of said experiment allowed to recollect only components having partition coefficients (stationary/mobile phase concentration) lesser than or equal to 1 due to the utilization of a flow of 10 ml/min and a running time of 80 minutes, from which, the last 40 minutes were carried out in extrusion mode.

This experiment revealed that the compounds which may possibly have activity were the least water soluble, since the activity increases in the fractions obtained in the extrusion mode, i.e. when the compounds were being extracted with the organic phase, Therefore, a second experiment was carried out with the same equipment but the flow and the quantity of *agave* syrup injected were raised in order to determine the process scalability and prove that the least water soluble compounds were the active compounds.

Figure 6:
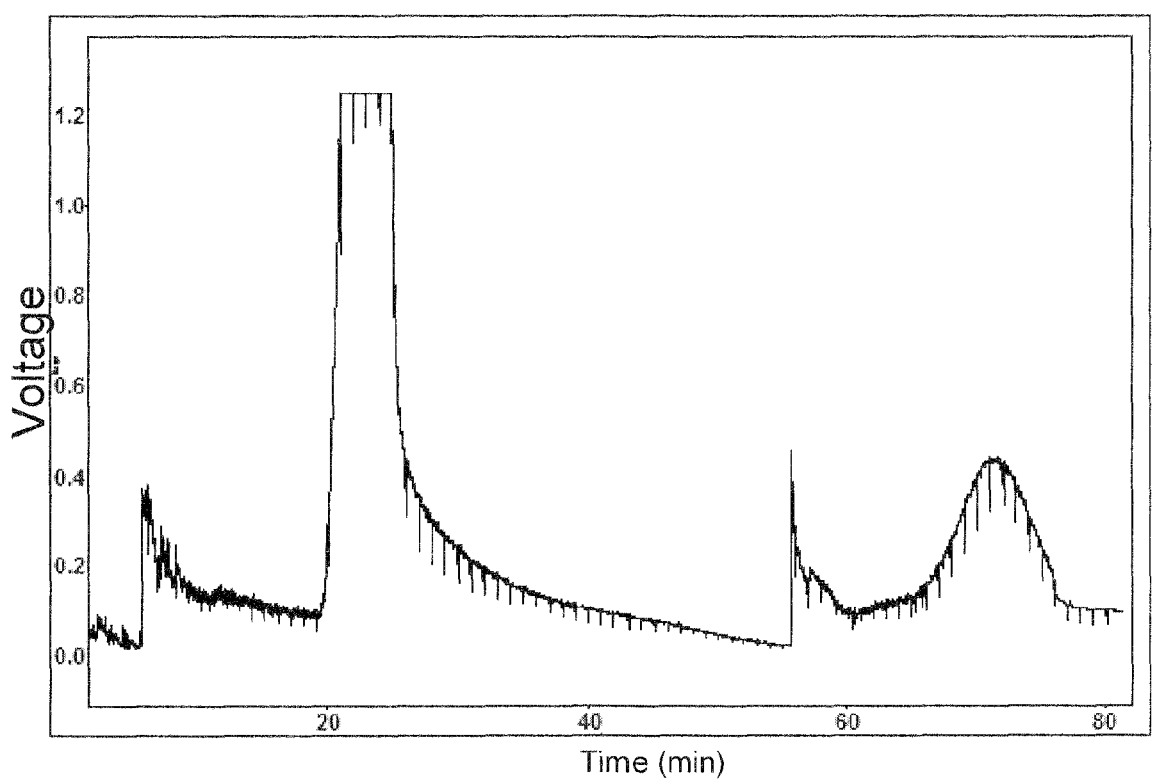
FIG. 6 comprises a graphic showing the chromatogram obtained from the separation of compounds by a fast centrifugal partition chromatography of an 80% methanolic extract of 10 g of *agave* syrup together with a solvent system comprised by water:ethyl acetate (92:2) and butanol:water ethyl acetate (47:13:40).

FIG. 6 shows the chromatogram of the fast centrifugal partition chromatography of 10 g of *agave* syrup diluted in 10 ml of the same mobile phase of the previous experiment. Once more, it was possible to separate the compounds contained in the *agave* syrup in two principal fractions. Furthermore, it was proved that the compound separation by fast centrifugal partition chromatography was scalable. Even though there was a rising in the quantity of *agave* syrup, the obtained partition coefficients were not affected in this experiment.

Figure 7:
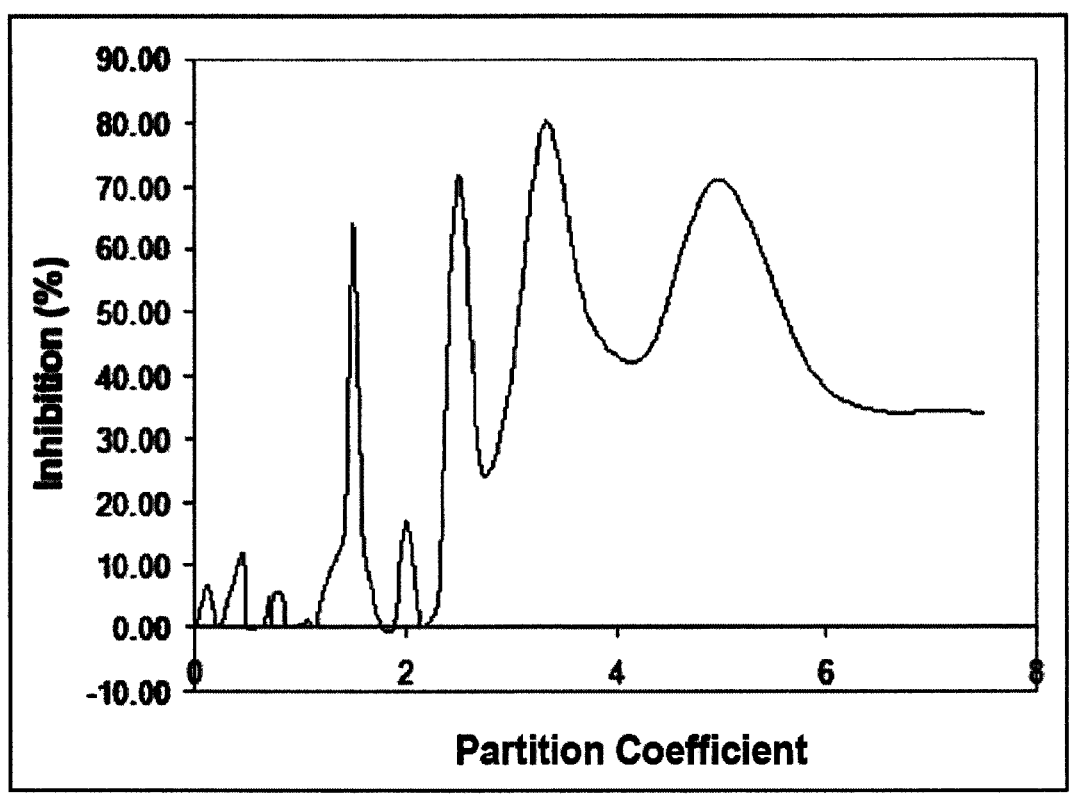
FIG. 7 comprises a graphic showing the growing inhibition over colon cancer cells of the fractions having different partition coefficient obtained by CPC at normal mode with extrusion in a two phase system comprised by water:ethyl acetate (92:8) and butanol:water:ethyl acetate (47:13:40).

In order to carry out a bioassay of the fractions, there were selected colon cancer cells in order to observe the inhibitory action of said fractions. FIG. 7 shows that the samples with the greatest partition coefficient were the samples that showed the greatest colon cancer cell inhibitory action.

EXAMPLE 6

Preliminary identification of the *agave* syrup active fraction components.

In order to carry out a tentative identification of the active components of the fraction obtained by CPC, it was analyzed by HPLC-MS. Using a column of $C_{18}$ (Zorbax 2.1×30 mm, 3.5 μm), the mobile phase comprised methanol and water which was modified with 5 mM of ammonium acetate at a flow of 0.5 ml/min. The column was balanced with 40% of methanol and a gradient was programmed in such way that, at a time of 12.5 minutes, the methanol percentage was incremented to 90% and maintained at said percentage during the last 5 minutes of the experiment. The temperature at which the separation was carried out was 40° C. and the chromatogram was obtained with positive ions between 50-1500 m/z which were detected by the ion trap.

Figure 8:
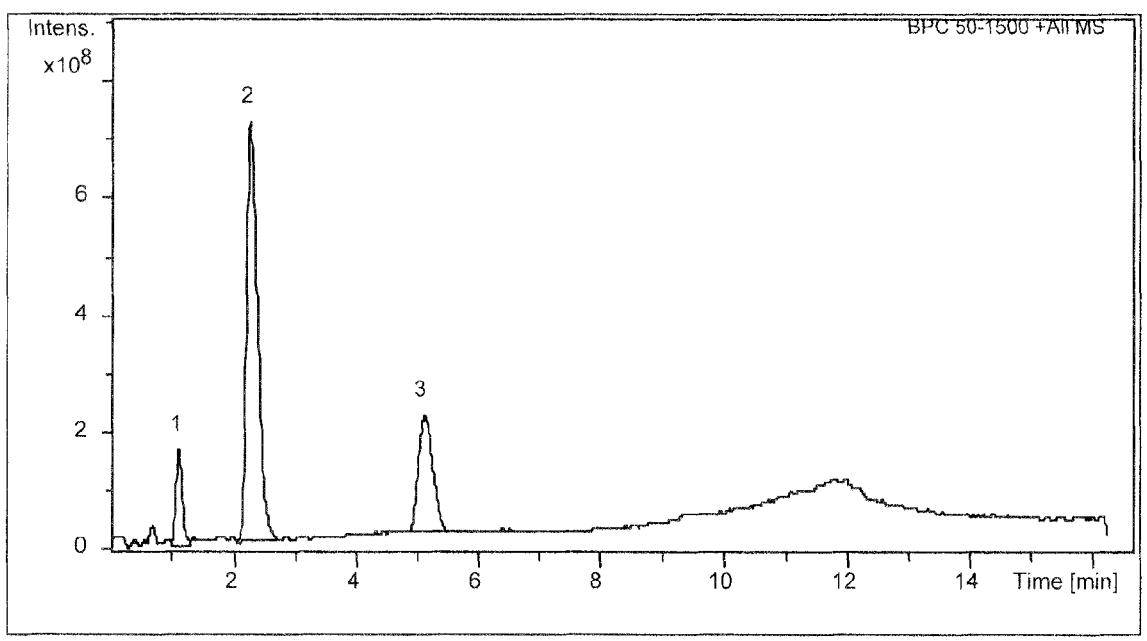
FIG. 8 comprises a graphic showing the chromatogram obtained by HPLC-MS of the fraction having the greater inhibitory effect of the experiment of FIG. 5.
Figure 9:
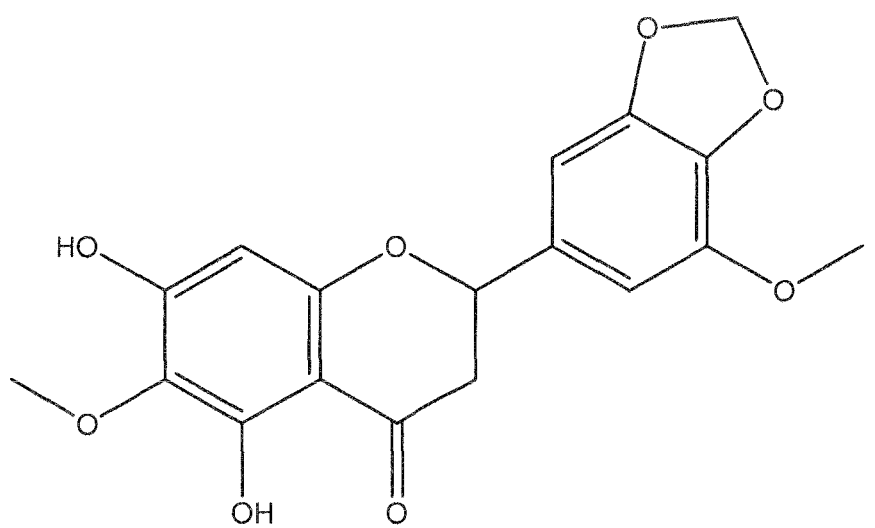
FIG. 9 show the chemical structure of agamenone (peak 3 of FIG. 7).
Figure 10:
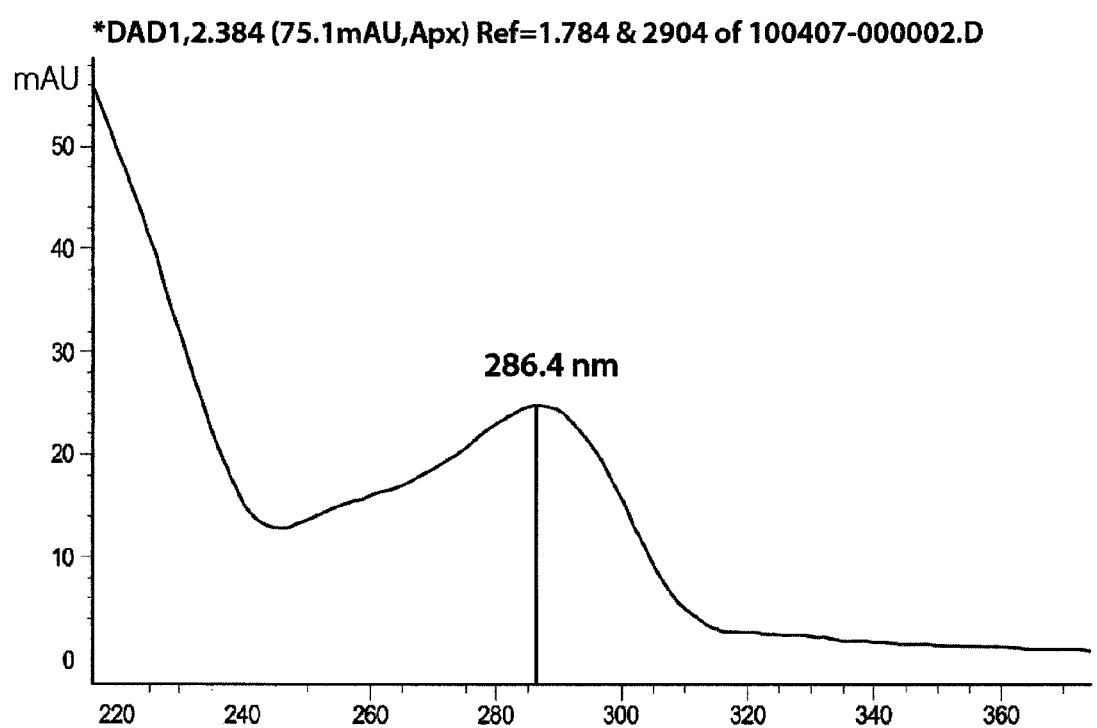
FIG. 10 shows the experimentally obtained $UV_{max}$ value of the agamennone structure or 5,7-Dihydroxy-6,5'-dimethoxy-3',4'-methylenedioxyflavanon.

FIG. 8 shows the presence of 3 main peaks in one of the most active fractions. The molecular mass of said two compounds do not coincide with any of the reported in the different *agave* species, except for the third peak. The third peak shown in FIG. 8 has a mass equal to the agamennone. FIG. 9 shows the agamennone structure or 5,7-Dihydroxy-6,5'-dimethoxy-3',4'-methylenedioxyflavanon whose reported $UV_{max}$ value match with the experimentally obtained value shown in FIG. 10. Furthermore, the spectrums of the other two present compounds coincide with the spectrum of a flavonol or an isoflavone and its positive ion masses are 304.3 and 332.3.

Finally it must be understood that the *agave* syrup extract having anticancerigen activity of the present invention, is not limited exclusively to the embodiments above described and illustrated and that the persons having ordinary skill in the art can, with the teaching provided by the invention, make modifications to the *agave* syrup extract having anticancerigen activity of present invention, which will clearly be within of the true inventive concept and of the scope of the invention which is claimed in the following claims.

The invention claimed is:

1. An *agave* extract comprising flavonoids, polycosanols and sapogenins that inhibit cancer cell growth over cells of liver and colon and provides the *agave* extract with antioxidant properties, wherein said *agave* extract has been extracted as a supernatant from an *agave* syrup which has been stored for at least eight weeks when the *agave* syrup is mixed with water and a substance selected from the group consisting of: methanol at a concentration of 80%, acetone at a concentration of 80% and ethanol at a concentration of 80% in order to promote an increase in the bioactivity of said phytochemicals.

2. The *agave* extract in accordance with claim 1, wherein the *agave* extract is extracted by:
   mixing said *agave* syrup with water and a substance selected from the group consisting of: methanol at a concentration of 80%, acetone at a concentration of 80% and ethanol at a concentration of 80%; and collecting supernatant extract, wherein said extract has an inhibitory cancer cell growth activity over colon and liver cancer cells.

3. The *agave* extract in accordance with claim 1, wherein the *agave* extract is extracted from an *agave* syrup which has been stored for at least eight weeks by:
   mixing said *agave* syrup with water and acetone at a concentration of 80% and collecting supernatant extract, wherein said extract has an inhibitory cancer cell growth activity over colon and liver cancer cells.

4. A method for producing an *agave* syrup having phytochemicals selected from the group comprising flavonoids, polycosanols and sapogenins, which provide anticancerigen and antioxidant properties to the *agave* syrup comprising: storing an *agave* syrup for at least eight weeks in order to promote an increase in bioactivity of said flavonoids, polycosanols and sapogenins.

5. A method for extracting an *agave* syrup extract comprising: mixing an *agave* syrup which has been stored for at least eight weeks with water and a substance selected from the group comprising: methanol at a concentration of 80%, acetone at a concentration of 80% and ethanol at a concentration of 80%; and collecting supernatant extract.

6. The method for extracting an *agave* syrup extract in accordance with claim 5 comprising: mixing an *agrave* syrup with water and acetone at a concentration of 80%; and collecting supernatant extract, wherein said extract has an inhibitory cancer cell growth activity, over colon and liver cancer cells.

7. A method for inhibiting growth of cancer cells, comprising administering to said cancer cells an *agrave* syrup extract having phytochemicals preferably selected from the group comprising flavonoids, polycosanols and sapogenins.

8. The method for inhibiting growth of cancer cells in accordance with claim 7, wherein the *agave* syrup extract is extracted from an *agave* syrup which has been stored for at least eight weeks.

9. The method for inhibiting growth of cancer cells in accordance with claim 7, wherein the *agave* syrup extract is extracted from an *agave* syrup which has been stored for at least eight weeks by mixing said *agave* syrup with water and a substance selected from the group comprising: methanol at a concentration of 80%, acetone at a concentration of 80% and ethanol at a concentration of 80%; and collecting supernatant extract.

10. The method for inhibiting the growth of cancer cells in accordance with claim 7, wherein the *agave* syrup extract is extracted from an *agave* syrup which has been stored for at least eight weeks by mixing said *agave* syrup with water and acetone at a concentration of 80%; and collecting supernatant extract wherein said extract has an inhibitory cancer cell growth activity, over colon and liver cancer cells.

* * * * *